United States Patent [19]

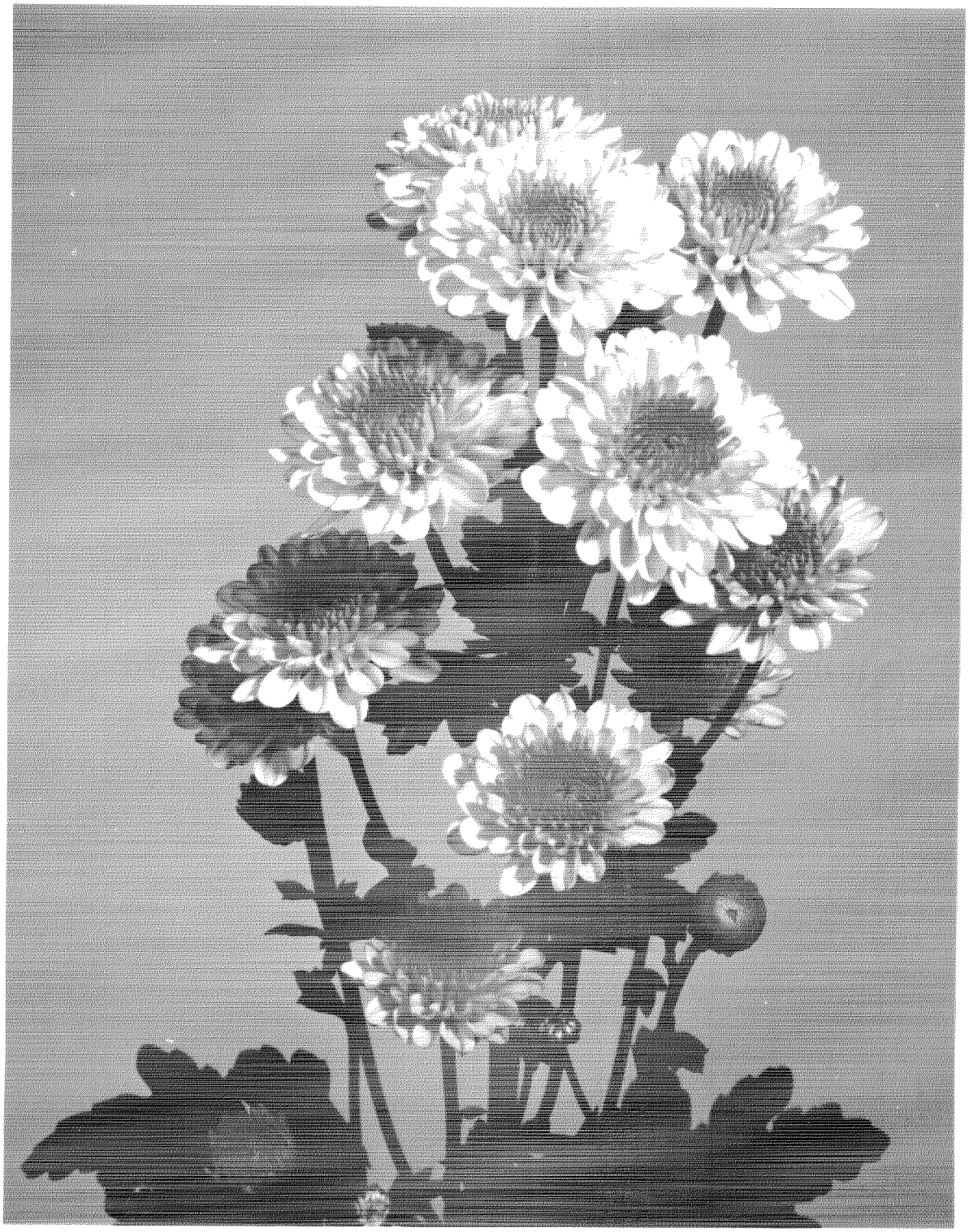

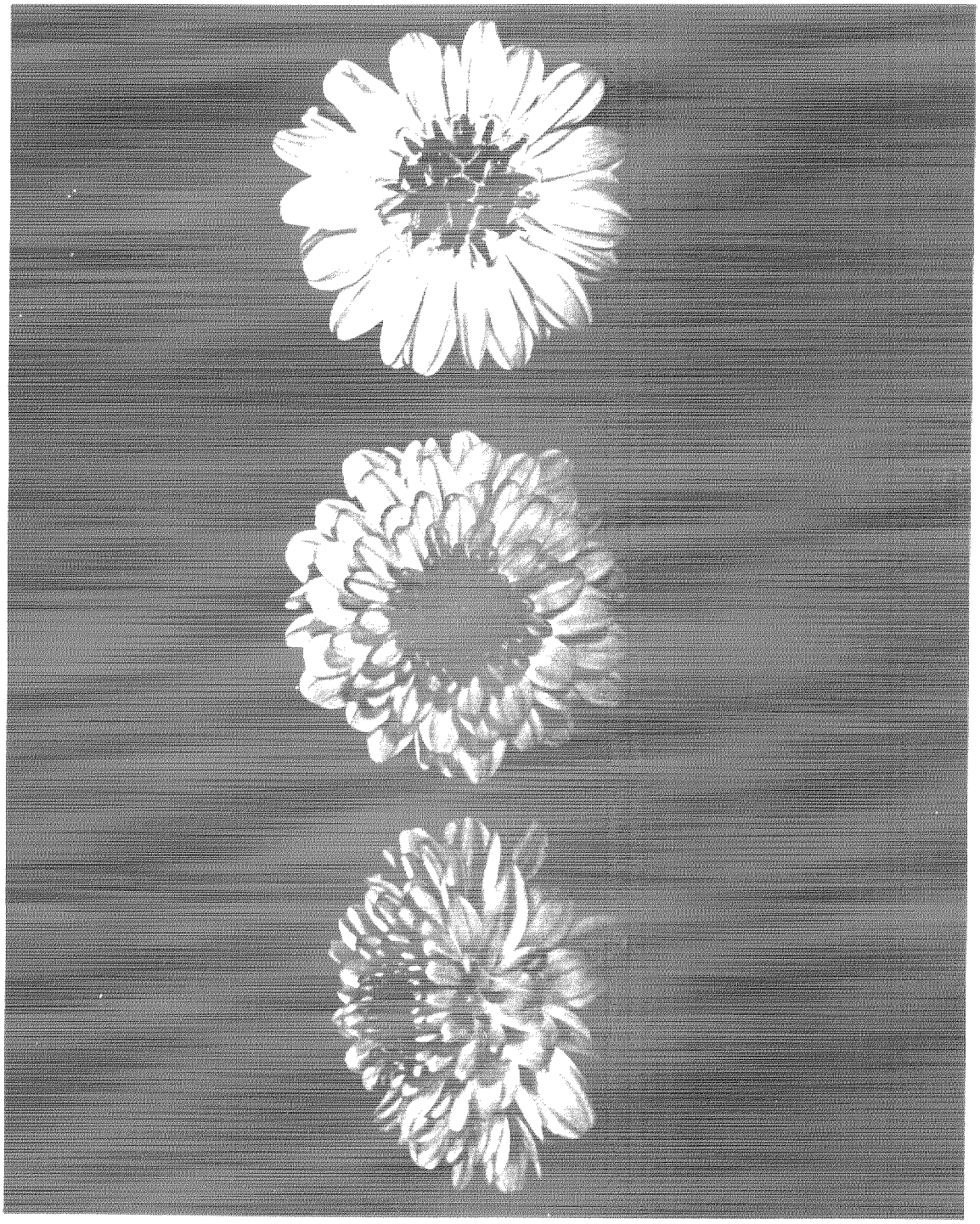

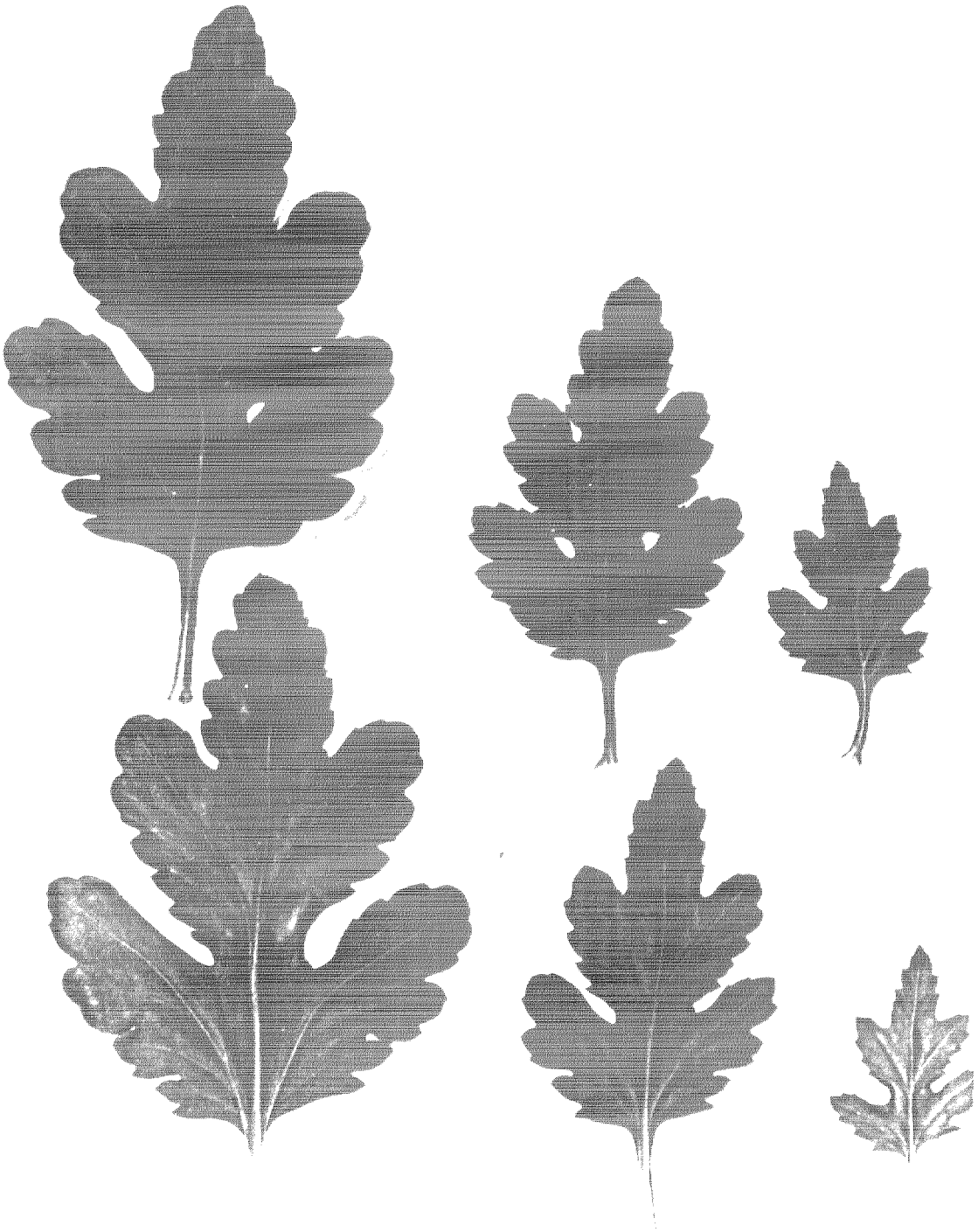

VandenBerg

[11] Patent Number: Plant 7,489

[45] Date of Patent: Apr. 2, 1991

[54] CHRYSANTHEMUM PLANT NAMED PASION

[75] Inventor: Cornelis P. VandenBerg, Salinas, Calif.

[73] Assignee: Yoder Brothers, Inc., Barberton, Ohio

[21] Appl. No.: 481,103

[22] Filed: Feb. 16, 1990

[51] Int. Cl.[5] ..... A01H 5/00

[52] U.S. Cl. ..... Plt./80

[58] Field of Search ..... Plt./76, 80, 81

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Pasion particularly characterized by its flat capitulum form; decorative capitulum type; light red-purple ray floret color; diameter across face of capitulum of 63 to 70 mm when fully opened; photoperiodic flowering response to short days of 50 to 58 days when grown in Salinas, Calif., and 64 to 70 days when grown in Bogota, Colombia; peduncle length of the first lateral of 5 to 10 cm, and of the fourth lateral of 10 to 18 cm, when grown without growth regulator applications, on open, terminal sprays; plant height of 102 to 107 cm when grown as a single stem spray cut mum in Salinas, Calif. with 14 long days prior to start of short days, compared to a height of 122 to 125 cm when grown in Bogota, Colombia with 20 to 21 long days prior to start of short days; and excellent tolerance to low night temperatures for bud initiation and flower development.

3 Drawing Sheets

1

The present invention comprises a new and distinct cultivar of Chrysanthemum, botanically known as *Dendranthema grandiflora*, and referred to by the cultivar name Pasion.

Pasion, identified as 85-251001, was originated by the inventor Cornelis P. VandenBerg from a cross made in a controlled breeding program in Salinas, Calif., in 1984.

The female parent of Pasion was an unnamed seedling identified as 81-772006, a yellow decorative cut spray mum. The male parent of Pasion was also an unnamed seedling identified as 78-*38002, a pink decorative cut spray mum.

Pasion was discovered and selected as one flowering plant within the progeny of the stated cross by Cornelis P. VandenBerg in March 1986, in a controlled environment in Salinas, Calif.

The first act of asexual reproduction of Pasion was accomplished when vegetative cuttings were taken from the initial selection in May 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Pasion are firmly fixed and are retained through successive generations of asexual reproduction.

Pasion has not been observed under all possible environmental conditions. The phenotype may vary significantly with variations in environment such as temperature, light intensity and daylength. For example, plant height will increase with an increased number of long days after planting prior to start of short days. Under low night temperatures (10 degrees Celsius and lower) flowering can be expected to be delayed. Under high temperatures (25 degrees Celsius night and 35 degrees Celsius day) flowering can be expected to be delayed and be more uneven than under normal temperatures. Normal temperatures can be described as 15 degrees Celsius minimum night and 25 degrees Celsius maximum day.

2

The following observations, measurements and comparisons describe plants grown in Salinas, Calif. and in Bogota, Colombia, under greenhouse conditions which approximate those generally used in commercial greenhouse practice. The low temperature tolerance was determined in repeated flowerings in Bogota, Colombia.

The following traits have been repeatedly observed and are determined to be basic characteristics of Pasion, which, in combination, distinguish this chrysanthemum as a new and distinct cultivar:

1. Flat capitulum form.
2. Decorative capitulum type.
3. Light red-purple ray floret color, with the center of the flowers being darker.
4. Diameter across face of capitulum of 63 to 70 mm when fully opened.
5. Flowering response in Salinas under normal temperatures is 50 to 58 days after start of short days. Flowering response in Bogota, Colombia under minimum 7 degrees Celsius night and maximum 29 degrees Celsius day is 64 to 70 days after start of short days.
6. Peduncle length of the first lateral at flowering after removing the apical bud without growth regulator applications is 5 to 10 cm when grown in Salinas, Calif., and 5 cm when grown in Bogota, Colombia. Peduncle length of the fourth lateral at flowering is 10 to 18 cm when grown in Salinas, and 10 to 13 cm when grown in Bogota.
7. Plant height of 102 to 107 cm when grown in Salinas as a single stem cut mum with 14 long days prior to start of short days; when grown in Bogota with 20 to 21 long days prior to start of short days height is 122 to 125 cm.
8. Excellent tolerance to low night temperatures for bud initiation and flower development. Average minimum low night temperatures in our Bogota trials ranged from 7 to 8.5 degrees Celsius.

The above measurements represent repeated flowerings over a period of a minimum of two years.

The accompanying photographic drawings show typical inflorescence and leaf characteristics of Pasion, with the colors being as nearly true as possible with illustrations of this type.

Sheet 1 is a color photograph of Pasion grown as a single stem cut spray mum.

Sheet 2 is a black and white photograph of three views of the inflorescence of Pasion.

Sheet 3 is a black and white photograph showing the upper and under sides of the leaves of Pasion at three stages of development (mature, intermediate and immature).

Of the commercial cultivars known to the inventor, the most similar in comparison to Pasion is the cultivar Hada, a red-purple spray cut mum disclosed in U.S. Plant Pat. No. 6,887. Reference is made to attached Chart A which compares certain characteristics of Pasion to the same characteristics of Hada.

Similar traits are capitulum form and type, spray formation, diameter across face of capitulum and low night temperature tolerance. Flowering response of Pasion has been generally similar to the response of Hada in Salinas trials, but has been slightly slower than the response of Hada in Bogota trials. Pasion has a unique two-tone flower color compared to the uniform single color of Hada. In general, the peduncle length of Pasion is shorter than the peduncle length of Hada. Since Pasion is normally grown with 7 more long days prior to short days than Hada, the plant height of both cultivars is not directly comparable.

In the following description color references are made to The Royal Horticultural Society Colour Chart. The color values were determined on plant material grown in Salinas, Calif. on July 17, 1989.

Classification:

*Botanical.*—*Dendranthema grandiflora* cv Pasion.

*Commercial.*—Decorative cut spray mum.

INFLORESCENCE

A. Capitulum:

*Form.*—Flat.

*Type.*—Decorative.

*Diameter across face.*—63 to 70 mm when fully opened.

B. Corolla of ray florets:

*Color (general tonality from a distance of three meters).*—Light red-purple, with a darker flower center.

*Color (upper surface).*—Outer petals 69A to 69B. Center of flower significantly darker, giving a two-tone effect. Center closest to 70C to 70D.

*Color (under surface).*—69A to 69B.

*Shape.*—Straight, oblong, slightly ribbed.

C. Corolla of disc florets:

*Color (mature).*—Closest to 12A.

*Color (immature).*—Closest to 144B.

D. Reproductive organs:

*Androecium.*—Present on disc florets only; no pollen.

*Gynoecium.*—Present on both ray and disc florets.

PLANT

A. General appearance:

*Height.*—102 to 107 cm when grown as a single stem cut mum with 14 long days prior to start of short days in Salinas, Calif.; 122 to 125 cm when grown as a single stem cut mum with 20 to 21 long days prior to start of short days in Bogota, Colombia.

B. Foliage:

*Color (upper surface).*—147A.

*Color (under surface).*—147B.

*Shape.*—See photograph.

CHART A

COMPARISON OF PASION AND HADA

| CHARACTERISTIC | PASION | HADA |
|---|---|---|
| Ray floret color | Light red-purple with darker center | Red-purple |
| Capitulum form | Flat | Flat |
| Capitulum type | Decorative | Decorative |
| Spray formation | Terminal | Terminal |
| Peduncle length | | |
| 1st lateral, Salinas | 5 to 10 cm | 8 to 10 cm |
| 4th lateral, Salinas | 10 to 18 cm | 13 to 15 cm |
| 1st lateral, Bogota | 5 cm | 8 to 13 cm |
| 4th lateral, Bogota | 10 to 13 cm | 15 to 18 cm |
| Diameter across face of capitulum | 63 to 70 mm | 63 to 70 mm |
| Flowering response period | | |
| in Salinas | 50 to 58 days | 54 to 57 days |
| in Bogota | 64 to 70 days | 62 to 67 days |
| Low night temperature tolerance | Excellent | Excellent |

COMPARISONS MADE OF PLANTS GROWN AS SINGLE STEM SPRAY CUT MUMS IN SALINAS, CALIFORNIA, AND IN BOGOTA, COLOMBIA

I claim:

1. A new and distinct Chrysanthemum plant named Pasion, as described and illustrated.

* * * * *